Figure 1:
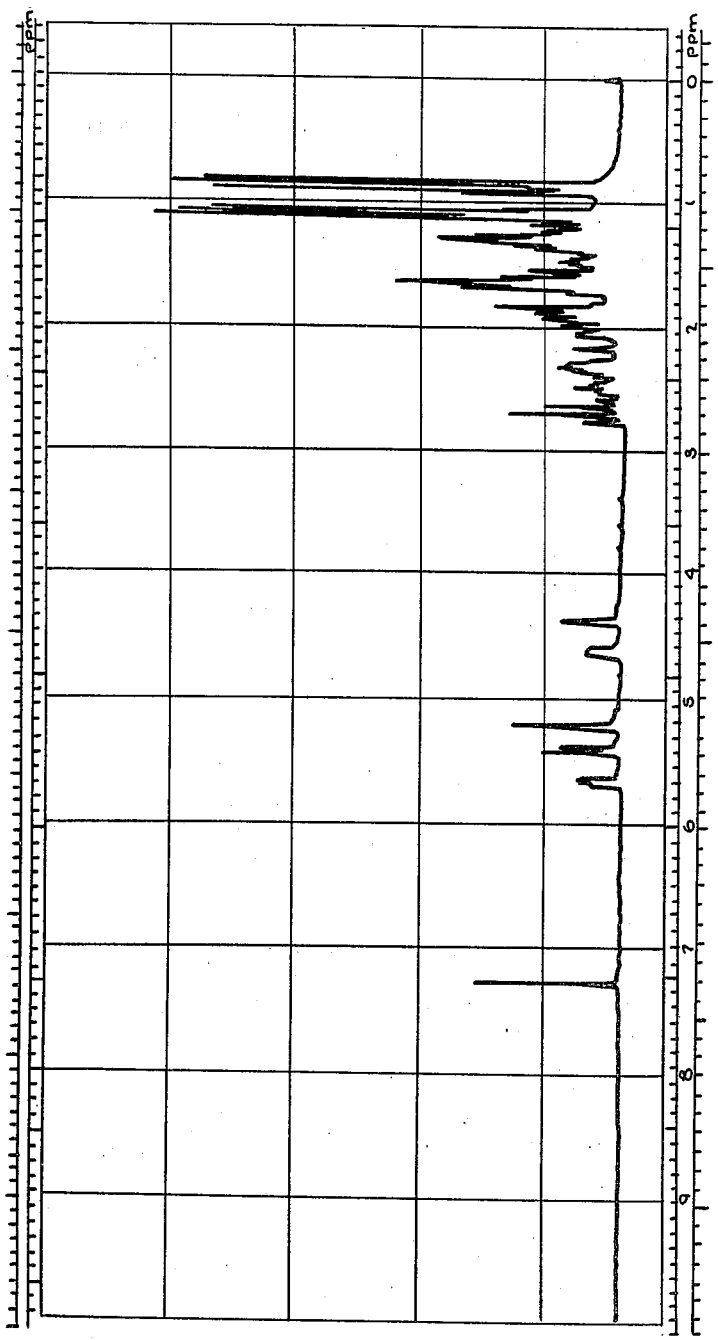

United States Patent

Albers-Schonberg et al.

[11] 4,420,491
[45] Dec. 13, 1983

[54] HYPOCHOLESTEREMIC FERMENTATION PRODUCTS AND PROCESS OF PREPARATION

[75] Inventors: George Albers-Schonberg, Princeton, N.J.; Henry Joshua, Staten Island, N.Y.; Maria B. Lopez, Elizabeth, N.J.

[73] Assignee: Merck & Co., Inc., Rahway, N.J.

[21] Appl. No.: 267,972

[22] Filed: May 28, 1981

Related U.S. Application Data

[60] Division of Ser. No. 154,157, May 28, 1980, Pat. No. 4,294,846, which is a continuation-in-part of Ser. No. 77,807, Sep. 21, 1979, abandoned.

[51] Int. Cl.$^3$ .................. C07C 69/28; C07C 69/76; A61K 31/22
[52] U.S. Cl. .................. 424/311; 560/119; 560/126; 560/256
[58] Field of Search .............. 560/126, 256, 119; 424/311, 305

[56] References Cited

U.S. PATENT DOCUMENTS

| | | | |
|---|---|---|---|
| 3,983,140 | 9/1976 | Endo et al. | 549/292 |
| 4,049,495 | 9/1977 | Endo et al. | 435/125 |
| 4,137,322 | 1/1979 | Endo et al. | 424/311 |
| 4,231,938 | 11/1980 | Monaghan et al. | 560/256 |
| 4,294,846 | 10/1981 | Albers-Schonberg et al. | 549/292 |

*Primary Examiner*—Natalie Trousof
*Assistant Examiner*—Patricia M. Scott
*Attorney, Agent, or Firm*—Wiliam H. Nicholson; Mario A. Monaco

[57] ABSTRACT

Substances isolated after cultivation of a microorganism belonging to the genus Aspergillus in a culture medium comprise compounds which have structures:

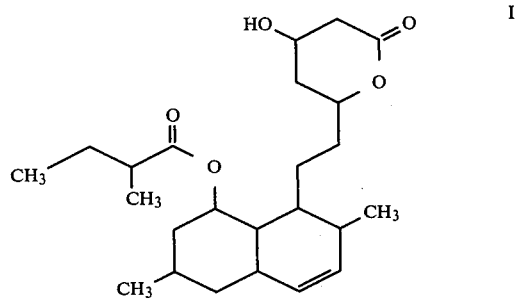

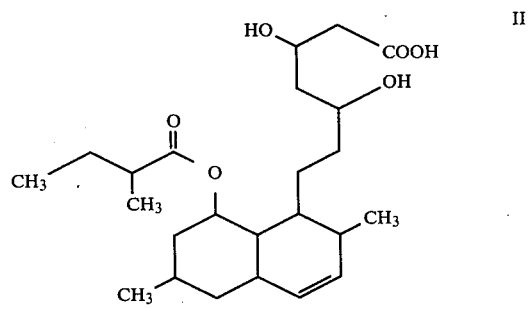

Together with salts and esters of the carboxylic acid, these compounds form a class of highly active hypocholesteremic and hypolipemic medicaments.

12 Claims, 2 Drawing Figures

HYPOCHOLESTEREMIC FERMENTATION PRODUCTS AND PROCESS OF PREPARATION

SUMMARY OF THE INVENTION

This is a division of application Ser. No. 154,157 filed May 28, 1980 (now U.S. Pat. No. 4,294,846), which is a continuation-in-part of application Ser. No. 077,807, filed Sept. 21, 1979 (abandoned).

This invention relates to hypocholesteremic products from the cultivation of a microfungus of the genus Aspergillus. More specifically, it relates to compounds of formulae I and II:

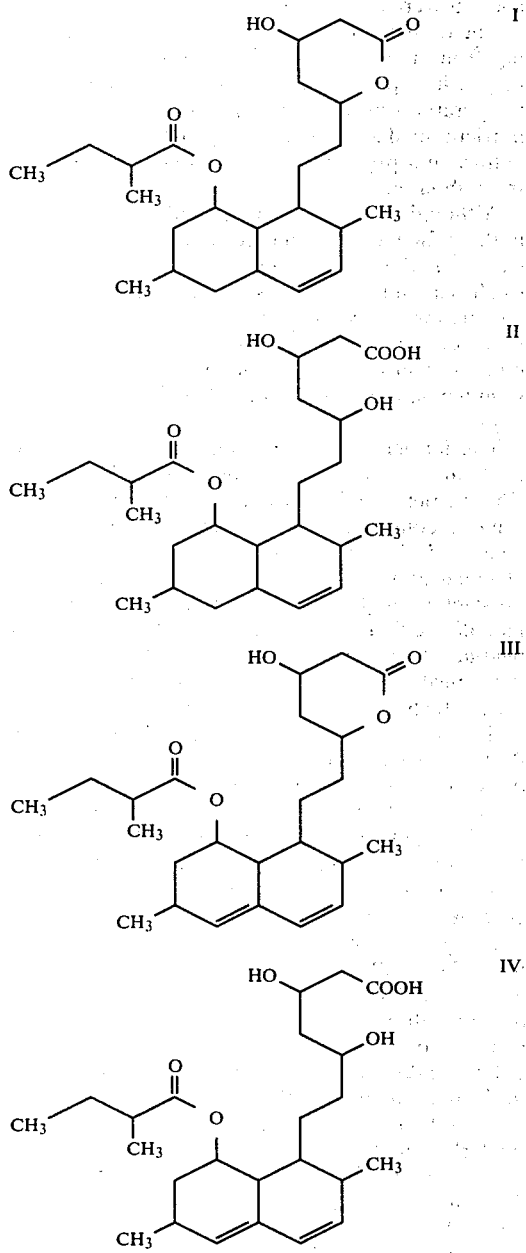

as well as pharmaceutically acceptable salts and lower alkyl and substituted alkyl esters of the carboxylic acids in which the possible substituent is phenyl, dimethylamino or acetylamino. Compounds III and IV are the subject of U.S. Pat. Nos. 4,231,938 and 4,342,767, respectively. The invention also relates to a process of cultivating the microfungus and isolating from the medium a hypocholesteremic compound of the above structures. These new compounds have excellent properties of inhibiting cholesterol biosynthesis and are useful against hypercholesteremia and hyperlipemia.

BACKGROUND OF THE INVENTION

Because of the possible connection between high blood cholesterol and atherosclerosis, many efforts have been made to find ways and substances which would reduce the cholesterol in the mammalian body. One of these ways is to inhibit in mammals the body's ability to synthesize cholesterol.

Recently, Endo et al., described (U.S. Pat. Nos. 4,049,495 and 3,983,140) a fermentation product obtained by cultivation of a microorganism of the genus Penicillium and isolation from the medium. They called it ML 236 B and determined its structure together with two relates compounds 236 A and 236 C. Its structure, under the name compactin, was also determined by A. G. Brown, T. C. Smale, T. J. King, $J. Chem. Soc.$ (Perkin I) 1165 (1975). This compound has been found to be an inhibitor, in vivo, of the biosynthesis of cholesterol.

DESCRIPTION OF THE INVENTION

It has been found that unexpectedly, the cultivation of a microorganism very different from that employed by Endo, a microfungus of the genus Aspergillus, produces new substances that are very potent inhibitors of the biosynthesis of cholesterol in mammals. We have found new compounds I and II among these substances which comprise principally the compounds I, II, III and IV, of the above structures, accompanied by only traces of other compounds. These new compounds, I and II, are much more potent inhibitors of cholesterol synthesis in vivo than is the compound, ML236B described by Endo.

The pharmaceutically acceptable salts of this invention include thoese formed from cations such as sodium, potassium, aluminum, calcium, lithium, magnesium, zinc, ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, tris(hydroxymethyl)aminomethane, and tetramethylammonium.

The compounds of this invention are highly useful as antihypercholesteremic agents for the treatment of atherosclerosis, hyperlipemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg. to 2000 mg. (preferably 2 to 100 mg) which may be given in two to four divided doses. Higher doses may be favorably employed as required.

The compounds of this invention also have useful antifungal activities. For example, they may be used to control strains of Penicillium sp., *Aspergillus niger,* Cladosporium sp., *Cochliobolus miyabeanus* and *Helminthosporium cynodnotis.* For those utilities they are admixed with suitable formulating agents, powders, emulsifying agents or solvents such as aqueous ethanol and sprayed or dusted on the plants to be protected.

In another aspect of this invention, it relates to a process for producing the compounds of this invention which comprises cultivating a microorganism belonging to the genus Aspergillus and then recovering said compounds of this invention from the cultured broth. Based upon taxonomic studies, this Aspergillus, isolated and identified as a hitherto undescribed microorganism, has been designated MF-4833 in the culture collection of Merck and Co., Inc., Rahway, N.J. and a culture thereof has been placed on permanent deposit with the American Type Culture Collection, 12301 Parklawn Drive, Rockville, Md. 20852, and has been assigned accession number ATCC 20541. Another sample, of a similar organism, designated MF-4845 in the Merck culture collection, has likewise been placed on deposit and has been given the accession number ATCC 20542. The latter organism is the one giving the better yield. Although the use of these is described in connection with the process of this invention, other organisms of the genus Aspergillus including mutants of the above ones are also capable of producing these novel compounds and their use is contemplated in carrying out the process of this invention.

The morphological characteristics of the microorganisms MF-4833 and MF-4845 have been found to be those of the genus Aspergillus. Using the criteria specified in the standard authority "Manual of the Aspergilli", Charles Thom and Kenneth B. Rasper, published by the Williams and Wilkins Company, Baltimore, Md., 1945, and by comparison with known species, it has been determined that both strains are *Aspergillus terreus*.

The culture of these organisms to produce the novel compounds is carried out in aqueous media such as those employed for the production of other fermentation products. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, ryes, cornstarch, corn meal and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include for example, yeast hydrolysates, primary yeast, soybean meal, cottonseed flour, hydrolysates of casein, corn steep liquor, distiller's solubles or tomato paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and are not intended to be limitative. Specifically, the carbon sources used in the culture media to produce the novel compounds of this invention included dextrose, dextrin, oat flour, oatmeal, molasses, citrate, soybean, oil, glycerol, malt extract, cod liver oil, starch, ethanol, figs, sodium ascorbate and lard oil. Included as nitrogen sources were peptonized milk, autolyzed yeast, yeast RNA, tomato paste, casein, primary yeast, peanut meal, distillers solubles, corn steep liquor, soybean mean, corn meal, NZ amine, beef extract, asparagine, cottonseed meal and ammonium sulfate. The major ionic components were $CaCO_3$, $KH_2PO_4$, $MgSO_4.7H_2O$ and $NaCl$ and small amounts of $CaCl_2.6H_2O$ and traces of Fe, Mn, Mo, B and Cu were also present.

The fermentation is carried out at temperatures ranging from about 20° to 37° C.; however, for optimum results it is preferable to conduct the fermentation at temperatures of from about 25° to 30° C. The pH of the nutrient media suitable for growing the Aspergillus culture and producing the novel compounds can vary from about 6.0 to 8.0.

Although the novel compounds are produced by both surface and submerged culture, it is preferred to carry out the fermentation in the submerged state. A small scale fermentation is conveniently carried out by inoculating a suitable nutrient medium with the Aspergillus culture and, after transfer to a production medium, permitting the fermentation to proceed at a constant temperature of about 28° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for 2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 28° C. This method of producing the novel compounds is particularly suited for the preparation of large quantities.

The compounds are conveniently isolated from the fermentation broth as the lactone (I) or as salts of Compound II.

Compound I can be hydrolyzed with bases such as NaOH to yield the salts such as the sodium salt of Compound II. The use of bases with other pharmaceutically acceptable cations affords salts of these cations. Careful acidification of the salts affords the hydroxy acid II. The hydroxy acid II or its ammonium salt can be converted to Compound I by refluxing in toluene. Treating Compound I under acidic or basic catalysis with methanol, ethanol, propanol, or butanol or with phenyl, dimethylamino, or acetylamine alkanols yields the corresponding esters of Compound II which also form a part of this invention.

A mixture of Compounds I and III can be conveniently isolated without the need for chromatography via the ammonium salt of Compounds II and IV. This isolation is convenient and more adapted to commercial use than is chromatography of the total broth extract. Salts of II are more active than Compound I in vitro in the inhibition of cholesterol biosynthesis and as antifungal agents. Therefore, these salts are one of the especially preferred dosage forms. Preferred salts, in addition to ammonium, include tetramethylammonium, and salts of ethylenediamine, sodium, potassium, calcium, N-methyl-glucamine, lysine, arginine and ornithine.

The physico-chemical properties of Compound I are summarized as follows:

1. Melting point: 129°–131° C.

2. Molecular Weight: 406.

3. Formula: $C_{24}H_{38}O_5$. Found by mass spectrometry: 406.2706; Calculated: 406.2719.

4. $^1$H NMR Spectrum: The spectrum was recorded in $CDCl_3$ solution and chemical shifts are shown in FIG. 1 in ppm relative to internal tetramethylsilane at zero ppm.

Figure 2:
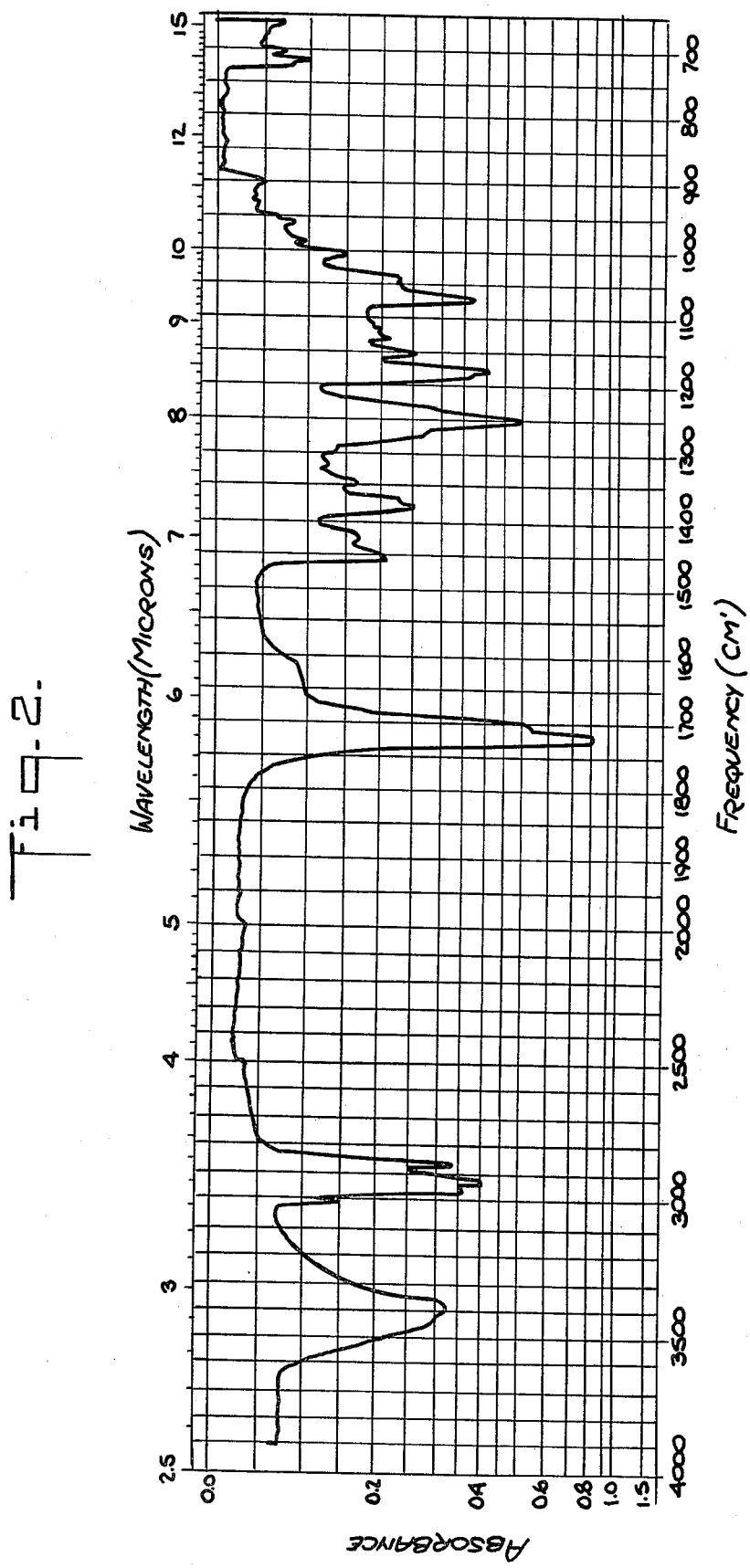

5. IR Spectrum: The infra red spectrum was recorded in a KBr pellet preparation of a sample. It is shown in FIG. 2.

6. Optical Rotation: The specific optical rotation is $[\alpha]_D^{25} = 148.6°$ (5.23 mg/ml $CH_3CN$).

7. $^{13}$C Nmr Chemical Shifts in $CDCl_3$: 11.8, 14.9, 16.5, 21.1, 23.1, 26.7(2C), 30.9, 31.3, 33.0, 35.7, 35.9, 37.4, 38.5, 38.6, 41.9(2C), 62.3, 70.1, 76.5, 131.0, 132.6, 171.2, 176.7.

8. UV Spectrum (in acetonitrile): End adsorption only.

On the basis of these and other data, the structure of the product is believed, with a considerable degree of certainty, to have the chemical structure:

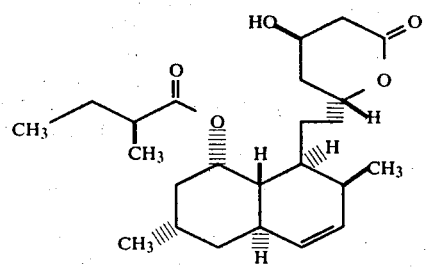

The corresponding hydroxy acid, Compound II, then, has the structure:

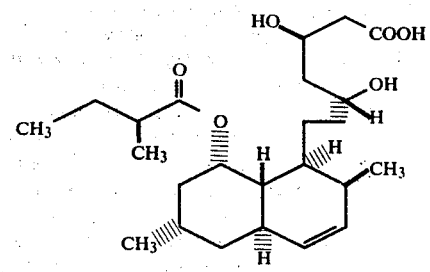

EXAMPLE 1

Preparation of Compounds I and II

A. Fermentation

A tube of lyophilized culture MF-4845 is opened aseptically and the contents suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 g |
| Distilled water | 1000 ml |
| pH 6.8 with NaOH | |
| Trace Element Solution: | |
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6Mo_7O_{24}.4H_2O$ | 19 mg |
| $ZnSO_4.7H_2O$ | 200 mg |
| Distilled Deionized Water | 1000 ml |

The inoculated flask is incubated for 24 hours at 28° C. on a 220 rpm shaker (2 inch throw). An unbaffled 2 liter Erlenmeyer flask containing 500 ml of the medium and then inoculated with 10 ml of the first stage fermentation growth from the seed mixture. This too was shaken 24 hours at 28° C.

A 200 gallon stainless steel fermentation vat was then charged with 485 liters of a medium comprising:

| Cerelose | 4.5% wt/vol |
|---|---|
| Peptonized Milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then 130 rpm for 84 hours at 28° C. with an air flow of 5 cfm for 12 hours then 10 cfm for 84 hours.

B. Isolation

1. Extraction

Two batches of one hundred gallons of whole broth were combined, acidified with stirring to pH4.1 by careful addition of 800 ml of concentrated hydrochloric acid, and extracted by addition of 75 gal of ethyl acetate and further stirring for two hours.

About 25 lbs of a siliceous filter aid was then added and the total slurry was pumped through a 24-inch filter press. An additional 75 gal of ethyl acetate was used to wash the press cake and continue the extraction, by reversing the direction of pumping through the press four times. Then all of the wash solvent was discharged from the press and combined with the first filtrate. The two-phase filtrate was allowed to settle, and the water layer removed. The ethyl acetate layer was washed with 10 gal of deionized water, the phases were allowed to separate and the ethyl acetate extracts were concentrated under vacuum to a residue of about 10 gal 2. Lactonization (In order to cyclize any Compound II in the extract to Compound I, the following azeotropic treatment was performed.)

Ethyl acetate extracts from an additional three hundred gal of broth were added to the above extract and the volume was reduced to about thirty gal by vacuum distillation. After fifty gal of toluene was added, and the batch was concentrated under vacuum to 32 gal; this step was repeated; then sufficient new toluene was added to bring the volume to 75 gal. Without vacuum, the batch was brought to reflux and maintained there for two hours, with a temperature over 106° C.

This solution was then concentrated under vacuum to a small volume, which was further concentrated to an oily residue in a large rotary evaporator under vacuum.

3. Chromatography on Silica Gel

The extract obtained above was flushed free of other solvents by addition of 2 gal of methylene chloride and reconcentration to an oil.

The oily residue was dissolved in about 5 gal of ethyl acetate-methylene chloride (30/70; v/v) mixture, and a slurry was made by addition of 2.8 kg of silica gel.

The slurry was loaded as a level layer on the top of a 12 in.×50 in. silica gel column packed in the same solvent mixture.

Elution was with ethyl acetate-methylene chloride (40/60; v/v) at 800 ml/min. A forerun of 10 gal, then further fractions of 4 gal each were collected.

Fractions 6-10 inclusive were concentrated under vacuum to an oily residue which was dissolved in hot ethyl acetate, treated with decolorizing carbon, filtered hot, and cooled. Crystals of Compound III were filtered off and the mother liquors were concentrated to an oil for further chromatography.

4. Rechromatography on Silica Gel

Mother liquor residues from similar broth extract work-ups equivalent to an additional 600 gal of fermentation production were combined with the above in methylene chloride solution. One-half of this solution was taken for further silica gel chromatography. A small aliquot showed a total solids content of 325 g. The solution was treated with 40 g of decolorizing carbon, filtered, and the cake rinsed with methylene chloride. The combined filtrate and washings were concentrated under vacuum to an oily residue. This was redissolved in 800 ml of ethyl acetate/methylene chloride (30/70; v/v) and slurried with 225 g of silica gel. The slurry was loaded on top of a 14×36 cm column bed of silica gel packed in the same solvent mixture. Development was with ethyl acetate/methylene chloride (40/60; v/v). A forecut of three liters was set aside; then fractions of 800 ml each were collected.

5. Chromatography on Reverse-phase Packing

Forty ml from fraction 12 of the above chromatography were concentrated to an oil weighing 500 mg and the oil redissolved in 5 ml acetonitrile. This acetonitrile solution was charged to a ⅜" OD by 6 ft long stainless steel chromatography column packed with preparative reverse-phase liquid chromatography column packing material "Bondapak C18/PorasilB" (Waters Associates, Inc., Milford, Mass. 01757). The column was eluted with a mixture consisting of v/v 55% acetonitrile and 45% 0.05 M ammonium phosphate pH3. The elution volume between 1360 ml and 1700 ml was combined on the basis of refractive index detection. The organic solvent was removed in vacuo and the residual aqueous solution extracted with ethyl acetate. In vacuo removal of the ethyl acetate left 120 mg of the title compound which crystallized from a concentrated acetonitrile solution yielding crystals Compound I, m.p. 129°-131° C.

EXAMPLE 2

Alternate Isolations via Ammonium Salts

The broth (100 gal) from a fermentation (Example 1A) is acidified with $H_3PO_4$ to pH of 5. Ethyl acetate (70 gal) is added and the mixture is stirred vigorously. It is then filtered from the mycelia residue and the cake is washed with a small amount of ethyl acetate which is combined with the main extract. The organic phase is separated and mixed with 5 gallons of 0.2 N sodium hydroxide solution. The mixture is stirred vigorously and then allowed to settle. The aqueous layer is separated and the pH is adjusted from 9 to 5 by addition of $H_3PO_4$. It is then extracted, first with 2 gallons of hexane-ethyl acetate 2:1 mixture and then with one gallon of the same mixture. The separate organic extracts are combined and dried over anhydrous $MgSO_4$. The drying agent is then separated by filtration and the cake washed with one liter of the same hexane-ethyl acetate solution, the rinse being combined with the filtrate. This filtrate solution, after further dilution with 2 L of acetone, is stirred while ammonia gas is passed in. The gas is absorbed and a crystalline precipitate appears. When ammonia is no longer absorbed, and a darkening in color is observed in the precipitate, the introduction of ammonia is terminated and the mixture is allowed to stand several hours after which it is filtered. The crude ammonium salt filter cake is washed with acetone to a colorless wash and is then air dried.

Crude ammonium salt, isolated as described, from a 1100 gal fermentation, is lactonized by dissolving in water, acidifying to pH3 with concentrated hydrochloric acid, extracting into toluene, and refluxing for two hours. Concentration under vacuum to a small volume affords crystals of crude Compound III mixed with a smaller amount of Compound I; these are filtered off and dried. Alternatively, the crude ammonium salts are refluxed in toluene under a stream of nitrogen until no more ammonia and water are separated (~2 hrs.). The hot solution is filtered and allowed to cool to room temperature, affording crystals of Compound III mixed with a smaller amount of Compound I. By either procedure successive concentration of the toluene mother liquor yield further crop of material of similar composition.

Material from twelve such batches is combined and recrystallized from 101 lbs of ethanol; the crystals of Compound III are filtered off and washed with ethanol. The combined mother liquors and washes are concentrated in vacuo to about 3 gal and a second crop of crystals of Compound III are filtered off. The mother liquors from this filtration are worked up as follows:

About 0.5 l of these mother liquors are prepared for reverse-phase chromatography by concentration under vacuum to remove ethanol, flushing with acetonitrile and filtration of trace insolubles. A solution in 100 ml of acetonitrile is passed quickly over a 200 ml bed of C-18 reverse-phase packing, and the bed washed with an additional liter of acetonitrile. The combined filtrates are concentrated and dissolved in a total of 360 ml of chromatographic solvent (60 acetonitrile-40 water v/v) and filtered to remove trace insolubles. Solids content by test aliquot is 15.3 g.

A charge of 160 ml of this feed stock is chromatographed in a Waters Prep 500 system using two 5×30 cm cartridges of C-18 reverse-phase packing (Waters Assoc.,; bonded octa decyl coating on silica) and acetonitrile-water, 60-40 (v/v) as the eluant at 130 ml/min, at ambient temperature, with refractive index detection. Impurities eluted in the first 3900 ml of eluant are rejected. A large peak of Compound III is obtained from 3900 to 5850 ml of eluant and set aside. Mixed fractions are obtained from 5850 ml to 6500 ml of elution; these are set aside for rechromatography. Purified Compound I is obtained as the last peak; the fraction between 6500 and 8450 ml of elution is collected and concentrated to an oily residue of about 3 g.

One-half (about 1.5 g) of this concentrate of Compound I is prepared for chromatography as the ammonium salt of Compound II by making a solution in 6 ml of warm methanol with agitation and adding immediately sufficient 1 N sodium hydroxide to hold the pH at 10.5–11; 3.5–3.8 ml of alkali are required. After standing for one-half hour, the solution is filtered to remove a trace of insolubles, and the filtrate is pumped into a column, 1″×34″ of 200-325 mesh milled XAD-2 resin (a styrene-divinylbenzene copolymer) and eluted with 23% acetonitrile −77% 0.1 N ammonium hydroxide (v/v) at 10 ml/min at 40° C. Fractions of 20 ml are collected; fractions 1 through 44 contain impurities, and a peak of Compound IV salt, which is rejected. Fractions 45–61 are collected, concentrated under vacuum to a small aqueous residual volume and freeze dried to a residue of ammonium salt of Compound II, wt. 0.72 g.

EXAMPLE 3

Alkali and Alkaline Earth Salts of Compound II

To a solution of 40 mg of the product of Example 1 in 2 ml of ethanol is added 1 ml of aqueous NaOH ($10^{-4}$ moles; 1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 4

Ammonium Salt of Compound II

The sodium salt from Example 3 is dissolved in 2 ml of water, cooled in ice and acidified slowly with 0.5 M HCl. The mixture is extracted with ethyl acetate, back-extracted with water, dried over $MgSO_4$ and filtered. The filtrate is treated with anhydrous ammonia with stirring and cooling to precipitate the ammonium salt.

EXAMPLE 5

Ethylenediamine Salt of Compound II

To a solution of 0.50 g of the ammonium salt of Compound II in 10 ml of methanol is added 75 μl of ethylenediamine. The methanol is stripped off under vacuum and the residue is triturated with acetone, stored in the cold, and filtered to obtain the ethylenediamine salt of Compound II.

EXAMPLE 6

Tris(hydroxymethyl)aminomethane Salt of Compound II

To a solution of 202 mg of the ammonium salt of Compound II in 5 ml of methanol is added a solution of 60.5 mg of tris(hydroxymethyl)aminomethane in 5 ml of methanol. The solvent is removed in vacuo and the residue triturated with a 1:1 mixture of acetonitrile:methanol. The desired tris(hydroxymethyl)aminomethane salt of Compound II is filtered off and dried.

EXAMPLE 7

L-Lysine Salt of Compound II

A solution of 0.001 mole of L-lysine and 0.0011 mole of the ammonium salt of Compound II in 15 ml of 85% ethanol is concentrated to dryness in vacuo. The residue is triturated with 10 ml of warm ethanol, cooled, and filtered to give the L-lysine salt of Compound II.

Similarly prepared are the L-arginine, L-ornithine, and N-methylglucamine salts of Compound II.

EXAMPLE 8

Tetramethylammonium Salt of Compound II

A mixture of 68 mg of Compound I in 2 ml of methylene chloride and 0.08 ml of 24% tetramethylammonium hydroxide in methanol is diluted with ether to cause precipitation of the tetramethylammonium salt of Compound II.

EXAMPLE 9

Preparation of Hydroxy Acid, Compound II

221 Mg of the ammonium salt of Compound II are dissolved in 4.5 ml of 65% ethanol, cooled in ice, acidified with about 0.5 ml of 1 M HCl to pH3, and evaporated at low temperature in a rotary evaporator to a volume of about 2 ml. 2 Ml more water are added, the mixture extracted into 2×3 ml of ethyl acetate, and backwashed with 1 ml of water, keeping all solutions cold in an ice bath. The extract is dried over $MgSO_4$ and evaporated to dryness in vacuo to obtain the hydroxy acid as a colorless oil.

A $^{13}C$-nmr spectrum in $CDCl_3$ exhibits chemical shifts for the first six carbons of the hydroxy acid part of the molecule as listed in the Table. Upon standing, this hydroxy acid slowly reverts to the lactone.

TABLE

13C-Nmr Spectrum in CDCl3, Ppm Downfield from Tetramethylsilane

| | | Hydroxy Acid, Compound IV |
|---|---|---|
| | $C_1$ | 175.0 |
| | $C_2, C_4$ | 42.2, 41.7 |
| | $C_3$ | 68.8 |
| | $C_5$ | 72.5 |
| | $C_6$ | 35.0 |

The spectrum of the remainder of the molecule is only slightly changed from the cyclized structure.

EXAMPLE 10

Ethyl Ester of Compound II

To a solution of 400 mg of the product, Compound I, in 100 ml of absolute ethanol is added 10 ml 0.1 M sodium ethoxide in absolute ethanol. This solution is allowed to stand at room temperature for one hour, is then diluted with water and extracted twice with water, the ethyl acetate dried over anhydrous sodium sulfate is removed in vacuo to yield the ethyl ester of Compound II.

In like manner, by the use of equivalent amounts of methanol, propanol, butanol, isobutanol, t-butanol, amylalcohol, isoamylalcohol, 2-dimethylaminoethanol, benzylalcohol phenethanol, 2-acetamidoethanol and the like, the corresponding esters are obtained.

EXAMPLE 10

A. In Vitro Inhibition of HMG Coenzyme A Reductase

The method of H. J. Knauss, *J. Biol. Chem.* 234 2835 (1959) was modified slightly by incubating the enzyme with the inhibitor for five minutes before initiating the reaction with the substrate. With potent inhibitors such as the novel compounds of this invention, the standard procedure of merely adding enzyme to the inhibitor-substrate mixture gave non linear kinetics.

Using the modified procedure, the sodium salt of Compound II gives an $IC_{50}$ in inhibiting HMG-CoA Reductase of $2.7 \times 10^{-9}$ M as compared with $5.4 \times 10^{-9}$ M for ML236B.

B. In Vivo Inhibition of Cholesterol Synthesis (Compound II)

Groups of male Holtzman rats were dosed with either 5% emulphor in saline or test compound in emulphor by stomack tube. After one hour 80 $\mu$Ci of $^{14}$C acetate/kg was given IP. The rats were bled 50 minutes later and $^{14}$C cholesterol was determined as a measure of sterol synthesis:

| Dose, mg/kg | % Inhibition |
|---|---|
| 0.15 | 38 |
| 0.6 | 51 |
| 1.2 | 70 |

EXAMPLE 11

Comparison of I and ML-236B as Inhibitors of Sterol Synthesis in Cell Culture The procedure of A. W. Alberts et al., *J. Biol. Chem.* 249: 5241 (1974) measuring the quantity of $^{14}$C sterol biosynthesis from $^{14}$C acetic acid in mouse L-M cells in culture was employed with modification. The test compound in 10 $\mu$l DMSO was added to the monolayer cultures with 5 $\mu$Ci of $^{14}$C acetate. After a 3 hour incubation, the cells were saponified and the $^{14}$C sterol extracted and isolated by thin layer chromatography on silica gel using petroleum ether-diethyl ether-acetic acid (75:25:1). The region on the plate containing $^{14}$C sterol was identified by staining with $I_2$ and the $^{14}$C content determined by liquid scintillation counting.

Using the modified procedure Compound I gives $IC_{50}$ in inhibiting HMG-CoA reductase of 17 nM as compared to 46 nM for ML-236B.

What is claimed is:

1. The compound:

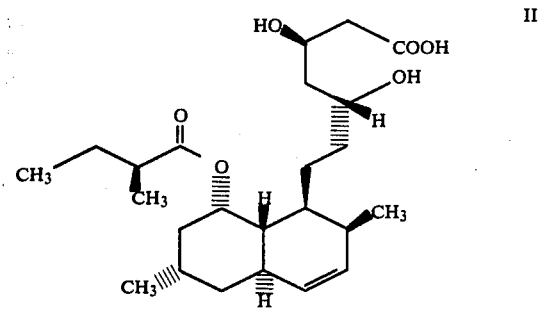

in substantially pure form or a pharmaceutically acceptable salt or a lower alkyl ester or a substituted lower alkyl ester wherein the substituent is phenyl, dimethylamino, or acetylamino.

2. The pharmaceutically acceptable salts of the compound of claim 1, wherein the cation is derived from ammonia, ethylenediamine, N-methylglucamine, lysine, arginine or ornithine.

3. The ammonium salt of Compound II of claim 1.

4. The ethylenediamine salt of Compound II of claim 1.

5. The lower alkyl esters and substituted lower alkyl esters of the compounds of claim 1.

6. The ethyl ester of Compound II of claim 1.

7. An antihypercholesterolemic pharmaceutical composition comprising a pharmaceutical carrier and an effective antihypercholesterolemic amount of the compound:

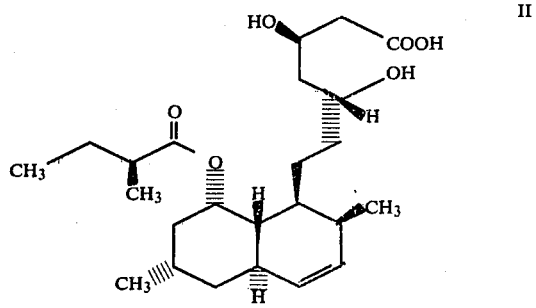

in substantially pure form or a pharmaceutically acceptable salt or a lower alkyl ester or a substituted lower alkyl ester wherein the substituent is phenyl, dimethylamino, or acetylamino.

8. The composition of claim 7 wherein the compound is a pharmaceuticaly acceptable salt wherein the cation is derived from ammonia, ethylenediamine, N-methylglucamine, lysine, arginine or ornithine.

9. The composition of claim 7 wherein the compound is the ammonium salt of Compound II.

10. The composition of claim 7 wherein the compound is the ethylenediamine salt of Compound II.

11. The composition of claim 7 wherein the compound is a lower alkyl ester or substituted lower alkyl ester.

12. The composition of claim 7 wherein the compound is the ethyl ester of Compound II.

* * * * *